United States Patent
Yamazaki et al.

(10) Patent No.: US 11,961,161 B2
(45) Date of Patent: Apr. 16, 2024

(54) INFORMATION PROCESSING APPARATUS, INFORMATION PROCESSING METHOD, AND STORAGE MEDIUM

(71) Applicant: CANON KABUSHIKI KAISHA, Tokyo (JP)

(72) Inventors: Fukashi Yamazaki, Kanagawa (JP); Kiyohide Satoh, Kanagawa (JP)

(73) Assignee: Canon Kabushiki Kaisha, Tokyo (JP)

( * ) Notice: Subject to any disclaimer, the term of this patent is extended or adjusted under 35 U.S.C. 154(b) by 402 days.

(21) Appl. No.: 17/157,699

(22) Filed: Jan. 25, 2021

(65) Prior Publication Data

US 2021/0150711 A1    May 20, 2021

Related U.S. Application Data

(63) Continuation of application No. PCT/JP2019/028475, filed on Jul. 19, 2019.

(30) Foreign Application Priority Data

Jul. 31, 2018   (JP) .................. 2018-143719

(51) Int. Cl.
  G06T 11/00   (2006.01)
  G06F 18/214  (2023.01)
  (Continued)

(52) U.S. Cl.
  CPC ............ G06T 11/00 (2013.01); G06F 18/214 (2023.01); G06F 18/2321 (2023.01);
  (Continued)

(58) Field of Classification Search
  CPC ............ G06T 11/00; G06T 7/0012; G06T 2207/20081; G06N 20/00; G06V 10/25;
  (Continued)

(56) References Cited

U.S. PATENT DOCUMENTS

| | | | |
|---|---|---|---|
| 10,657,444 B2 * | 5/2020 | Harvey | G06F 18/214 |
| 2008/0219529 A1 * | 9/2008 | Alexandrov | G06V 10/771 |
| | | | 382/128 |

(Continued)

FOREIGN PATENT DOCUMENTS

| | | |
|---|---|---|
| CN | 108288064 A | 7/2018 |
| JP | 2006-48370 A | 2/2006 |

(Continued)

OTHER PUBLICATIONS

Ronneberger, O., et al., "U-Net: Convolutional Networks for Biomedical Image Segmentation", MICCAI 2015, pp. 234-241.

*Primary Examiner* — David Bilodeau
(74) *Attorney, Agent, or Firm* — Canon U.S.A., Inc., IP Division

(57) ABSTRACT

An information processing apparatus according includes an acquisition unit configured to acquire an image, an extraction unit configured to extract part of regions included in the image as a target region, a determination unit configured to determine a variation in density value of a pixel included in the target region such that an absolute value of the variation in density value of the pixel included in the target region is larger than an absolute value of a variation in density value of a pixel included in a region other than the target region, a generation unit configured to generate a training image in which a density value of the pixel included in the target region is changed based on the variation determined by the determination unit, and a training unit configured to train a identifier using the training image.

18 Claims, 12 Drawing Sheets

(51) Int. Cl.
  *G06F 18/2321*  (2023.01)
  *G06N 20/00*  (2019.01)
  *G06T 7/00*  (2017.01)
  *G06V 10/25*  (2022.01)
  *G06V 10/774*  (2022.01)

(52) U.S. Cl.
  CPC ........... *G06N 20/00* (2019.01); *G06T 7/0012* (2013.01); *G06V 10/25* (2022.01); *G06V 10/774* (2022.01); *G06T 2207/20081* (2013.01)

(58) Field of Classification Search
  CPC .. G06V 10/774; G06F 18/214; G06F 18/2321
  See application file for complete search history.

(56) References Cited

U.S. PATENT DOCUMENTS

| | | | | |
|---|---|---|---|---|
| 2014/0244304 | A1* | 8/2014 | Lynn | G16H 10/60 |
| | | | | 705/3 |
| 2019/0272651 | A1* | 9/2019 | Lynn | G16H 40/67 |
| 2020/0005472 | A1 | 1/2020 | Terunuma et al. | |
| 2021/0358126 | A1* | 11/2021 | Goto | G16H 50/20 |

FOREIGN PATENT DOCUMENTS

| | | | |
|---|---|---|---|
| JP | 2013-122723 | A | 6/2013 |
| JP | 2018-089065 | A | 6/2018 |
| JP | 2019175093 | A | 10/2019 |
| WO | 2007/029467 | A1 | 3/2007 |
| WO | 2018/159775 | A1 | 9/2018 |

\* cited by examiner

FIG.8

| AVERAGE DENSITY VALUE m | INCREASE/DECREASE VALUE OF DENSITY VALUE |
|---|---|
| ⋮ | ⋮ |
| $-30 \leq m < -20$ | +10, +20, +30, +40, +50, +60 |
| ⋮ | ⋮ |
| $0 \leq m < +10$ | -30, -20, -10, +10, +20, +30 |
| $+10 \leq m < +20$ | -40, -30, -20, -10, +10, +20 |
| ⋮ | ⋮ |

INFORMATION PROCESSING APPARATUS, INFORMATION PROCESSING METHOD, AND STORAGE MEDIUM

CROSS-REFERENCE TO RELATED APPLICATIONS

This application is a Continuation of International Patent Application No. PCT/JP2019/028475, filed Jul. 19, 2019, which claims the benefit of Japanese Patent Application No. 2018-143719, filed Jul. 31, 2018, both of which are hereby incorporated by reference herein in their entirety.

BACKGROUND OF THE INVENTION

Field of the Invention

The disclosure of the present specification relates to an information processing apparatus, an information processing method, and a storage medium.

Background Art

In recent years, machine learning has been used in the field of image recognition. Performing image recognition using a identifier based on the machine learning requires a set of a training image and ground truth data, which is called training data. Density values of a target object drawn as an image usually fluctuate in accordance with various conditions at the time of image capturing. Thus, a massive amount of training data needs to be prepared to include all density values that can be taken by the target object in an actual image. In view of this issue, Patent Literature 1 discusses a method of performing affine transformation (scaling and rotation) and attribute conversion (brightness, contrast, and edge strength) on training data belonging to a class that has a small number of images to generate new training data.

CITATION LIST

Patent Literature

PTL 1: Japanese Patent Application Laid-Open No. 2006-48370

However, the method described in Patent Literature 1 uniformly changes density values of the training data, which is not preferable in some cases.

SUMMARY OF THE INVENTION

The disclosure of the present specification is directed to training a identifier using new training data whose density values have been appropriately changed, as one of targets of the disclosure.

The targets of the disclosure of the present specification are not limited to the above. Achieving other actions and effects that can be derived from each constituent element described in exemplary embodiments to implement the invention, which will be described below, and that cannot be obtained by conventional technologies can also be positioned as one of other targets of the disclosure of the present specification.

An information processing apparatus according to the disclosure of the present specification includes an acquisition unit configured to acquire an image, an extraction unit configured to extract part of regions included in the image as a target region, a determination unit configured to determine a variation in density value of a pixel included in the target region such that an absolute value of the variation in density value of the pixel included in the target region is larger than an absolute value of a variation in density value of a pixel included in a region other than the target region, a generation unit configured to generate a training image in which a density value of the pixel included in the target region is changed based on the variation determined by the determination unit, and a training unit configured to train a identifier using the training image.

Further features of the present invention will become apparent from the following description of exemplary embodiments with reference to the attached drawings.

BRIEF DESCRIPTION OF THE DRAWINGS

FIG. 8 is a diagram illustrating an example of a correspondence table to determine a variation in density value in the information processing apparatus according to the second exemplary embodiment.

DESCRIPTION OF THE EMBODIMENTS

Figure 1:
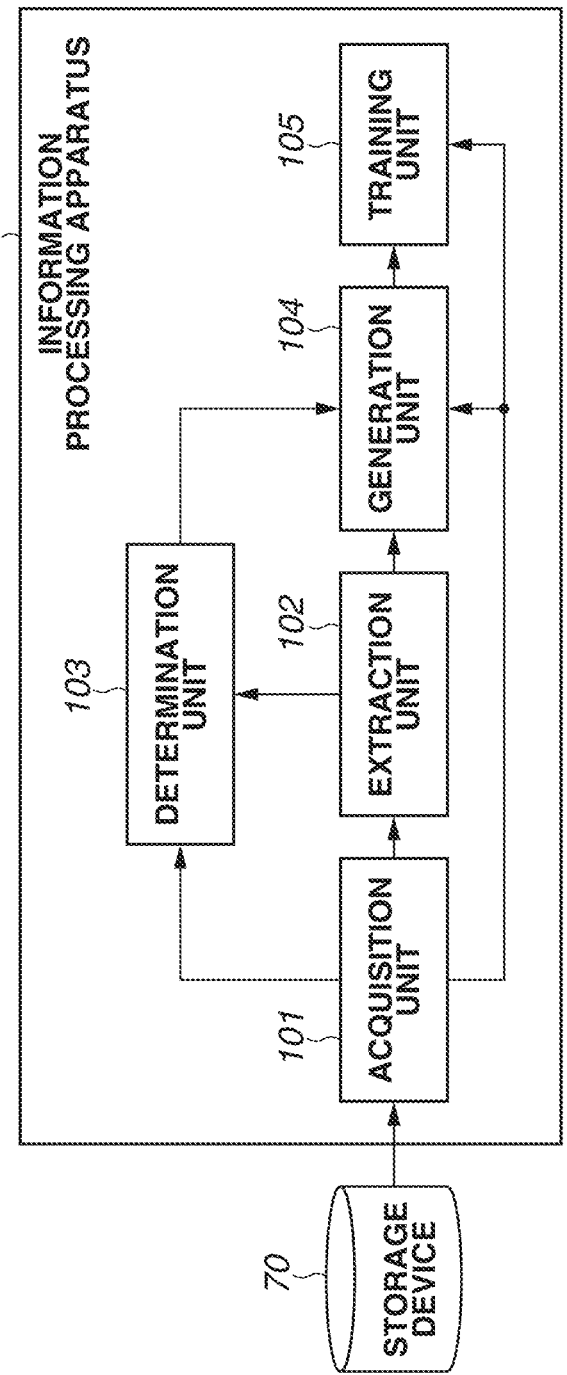
FIG. 1 is a diagram illustrating a configuration example of an information processing apparatus according to a first exemplary embodiment.

An information processing apparatus according to exemplary embodiments appropriately determines different variations in density value with respect to a plurality of regions in an image on the basis of characteristics of an object whose image is captured, an image capturing condition, or the like. The information processing apparatus then performs density value conversion of the image on the basis of the variations in density value determined with respect to the respective regions to generate new training data whose density values have been appropriately changed. Regarding the information processing apparatus according to the present exemplary embodiment, a description will be given of processing on a three-dimensional tomographic image (one type of a three-dimensional image) of the human body imaged by an X-ray computed tomography (X-ray CT) apparatus. However, the scope of application of the disclosure of the present specification is not limited to the three-dimensional tomographic image captured by the X-ray CT apparatus described above. For example, the disclosure of the present specification may employ a three-dimensional tomographic image captured by a nuclear magnetic resonance imaging apparatus (magnetic resonance imaging (MRI) apparatus), a positron emission tomography (PET) apparatus, or a three-dimensional ultrasonic imaging apparatus. Besides these images, the disclosure of the present specification may employ any image that has a region whose density value is varied and a region whose density value is not varied in accordance with a change in image capturing condition. In addition, the disclosure of the present specification can also be applied to a two-dimensional image (for example, a plain X-ray image) besides the three-dimensional image. Specifically, the disclosure of the present specification can also be applied to an electron beam CT image or a natural image besides the plain X-ray image. Assume that an automobile is a target of density conversion in a natural image such as a captured image of a traffic situation. In this case, conceivable application of the disclosure of the present specification is to vary a density value of the automobile in the image and not to vary a density value of a road or a sign. The density value of the road or sign may be varied with a more minute variation in density value than a variation in density value of the automobile. Alternatively, the density value of the automobile may be varied with a more minute variation in density value than a variation in density value of the road or sign. That is, a density value of a pixel included in a first region in the image may be changed such that an absolute value of a variation in density value of the pixel included in the first region is larger than an absolute value of a variation in density value of a pixel included in a second region that is different from the first region. The above is merely an example, and the image is not limited to the above and only needs to be an image in which different variations in density value are preferably set to a plurality of regions on the basis of the characteristics of the object whose image is captured, the image capturing condition, or the like.

A description will be given of a identifier that extracts a region of an object from an image as an example of performing image recognition by the identifier based on machine learning. More specifically, the present exemplary embodiment will be described using an example of a convolutional neural network (CNN) that performs region extraction of a lung field with respect to the three-dimensional tomographic image captured by the X-ray CT apparatus. The region extraction mentioned herein represents processing of dividing the image into a region of interest and a region other than the region of interest. The region extraction is also called as region division, image division, or segmentation in the field of image processing.

As one example of the CNN that performs the region extraction of the lung field, the present exemplary embodiment uses U-Net [O. Ronneberger et al., "U-Net: Convolutional Networks for Biomedical Image Segmentation", Medical Image Computing and Computer-Assisted Intervention (MICCAI), vol. 9351: 234-241, 2015]. In training of the U-Net, a two-dimensional tomographic image (one image out of a plurality of tomographic images constituting a three-dimensional tomographic image), which is a training image, and ground truth data corresponding to the two-dimensional tomographic image constitute training data. The ground truth data according to the present exemplary embodiment is, for example, a mask image representing a lung field region. The mask image is an image in which whether a pixel is a pixel belonging to the region of interest is represented in binary.

A description will be given below of the identifier that extracts a region of an object, but the scope of application of the disclosure of the present specification is not limited thereto. For example, the disclosure of the present specification may employ an identifier that detects the position of the object, an identifier that classifies the object on the basis of what the object is, or an identifier that analyzes in what state the object is. Besides these identifiers, the disclosure of the present specification may employ any identifier that performs image recognition.

First Exemplary Embodiment

The information processing apparatus according to a first exemplary embodiment divides each training image included in training data into two regions, i.e., a region whose density value is changeable in accordance with the characteristics of the object whose image is captured, the image capturing condition, or the like, and a region whose density value is nearly unchanged in accordance with the characteristics of the object whose image is captured, the image capturing condition, or the like. The information processing apparatus then changes (increases/decreases) a density value of a pixel belonging to the region whose density value is changeable by a predetermined method (which will be described below). On the other hand, the information processing apparatus does not change a density value of a pixel belonging to the region whose density value is nearly unchanged. With such a method, the information processing apparatus generates a new training image from each training image originally included in the training data (hereinafter referred to as an original image). The information processing apparatus brings each newly generated training image into correspondence with ground truth data in correspondence with the original training image (original image) as a set. The information processing apparatus adds this set of the newly generated training image and the ground truth data to the training data. Finally, the information processing apparatus performs training of the identifier using the newly structured training data.

In the following example, a human body region (excluding the lung field region) in the training image is assumed as the region whose density value of the image is changeable. An air region is assumed as the region whose density value is nearly unchanged. The reason for assuming the human body region (excluding the lung field region) as the region whose density value of the image is changeable is that this region is drawn with different density values in accordance with an individual difference among subjects being tested or an image capturing condition. The image capturing condition mentioned herein represents, for example, a condition regarding the X-ray CT apparatus such as a tube voltage, or whether a contrast agent has been administered. In the air region, the density value is nearly unchanged (the air: −1000 HU) even if the image capturing condition is changed. For this regions, determination with respect to such regions is a preferable example in the present exemplary embodiment.

In the following description, a region assumed as the region whose density value of the image is changeable in the original image is referred to as a target region whose density value is to be changed. A region assumed as the region whose density value of the image is almost unchanged in the original image is referred to as a region other than the target region. In addition, a region extracted by the identifier that has been trained by the technology of the disclosure of the present specification is referred to as a region as a target of region extraction by the identifier, or a region of interest. In the present exemplary embodiment, the lung field region is the region as the target of the region extraction.

A functional configuration example of an information processing system according to the present embodiment will be described below with reference to FIG. 1. As illustrated in FIG. 1, an information processing apparatus 100 according to the present exemplary embodiment is composed of an acquisition unit 101, an extraction unit 102, a determination unit 103, a generation unit 104, and a training unit 105. In addition, the information processing system according to the present exemplary embodiment includes a storage device 70 outside the information processing apparatus 100.

The storage device 70 is an example of a computer-readable storage medium, and is a high-capacity information storage device typified by a hard disk drive (HDD) or a solid state drive (SSD). The storage device 70 holds at least one or more original images (three-dimensional tomographic images). In addition, the storage device 70 holds ground truth data corresponding to each original image. The original image and ground truth data held by the storage device 70 are input to the information processing apparatus 100 via the acquisition unit 101. The ground truth data according to the present exemplary embodiment is a ground truth image of the lung field region, and is a mask image representing whether a pixel is a pixel belonging to the lung field region in binary. In this mask image, a pixel value of the region of interest is represented as 1, and a pixel value of the region other than the region of interest is represented as 0. In addition, the mask image has the same image size as the original image. Any pixel value, from which a pixel representing the region of interest and a pixel representing the region other than the region of interest can be discriminated, may be allocated to the pixel value in the mask image. For example, either one of 1 or 2 may be allocated to the pixel value. Alternatively, two values out of three or more values may be allocated. Still alternatively, the mask image may be of the same size as the original image, or may be of an image size different from that of the original image.

Each unit constituting the information processing apparatus 100 will be described below.

The acquisition unit 101 acquires training data (a set of the original image and the ground truth data in correspondence with the original image) from the storage device 70. The acquisition unit 101 then transmits the acquired original image to the extraction unit 102, the determination unit 103, the generation unit 104, and the training unit 105. In addition, the acquisition unit 101 transmits the acquired ground truth data to the training unit 105.

The extraction unit 102 extracts the target region whose density value is to be changed from the image acquired from the acquisition unit 101. The extraction unit 102 then transmits information of the extracted target region to the generation unit 104. The information of the target region mentioned herein is, for example, the mask image representing the target region whose density value is to be changed.

The determination unit 103 determines a variation in density value on the basis of the image acquired from the acquisition unit 101 and the information of the target region acquired from the extraction unit 102. The determination unit 103 then transmits the determined variation in density value to the generation unit 104.

The generation unit 104 generates a new training image on the basis of the image acquired from the acquisition unit 101, the information of the target region acquired from the extraction unit 102, and the variation in density value acquired from the determination unit 103. The generation unit 104 then transmits the generated training image to the training unit 105.

The training unit 105 trains the identifier on the basis of the image and ground truth data acquired from the acquisition unit 101 and the training image acquired from the generation unit 104.

At least part of the units of the information processing apparatus 100 in FIG. 1 may be implemented as independent devices. Alternatively, the units of the information processing apparatus 100 may be implemented as software to execute respective functions of the units. In the present exemplary embodiment, assume that the units are implemented as software.

Figure 2:
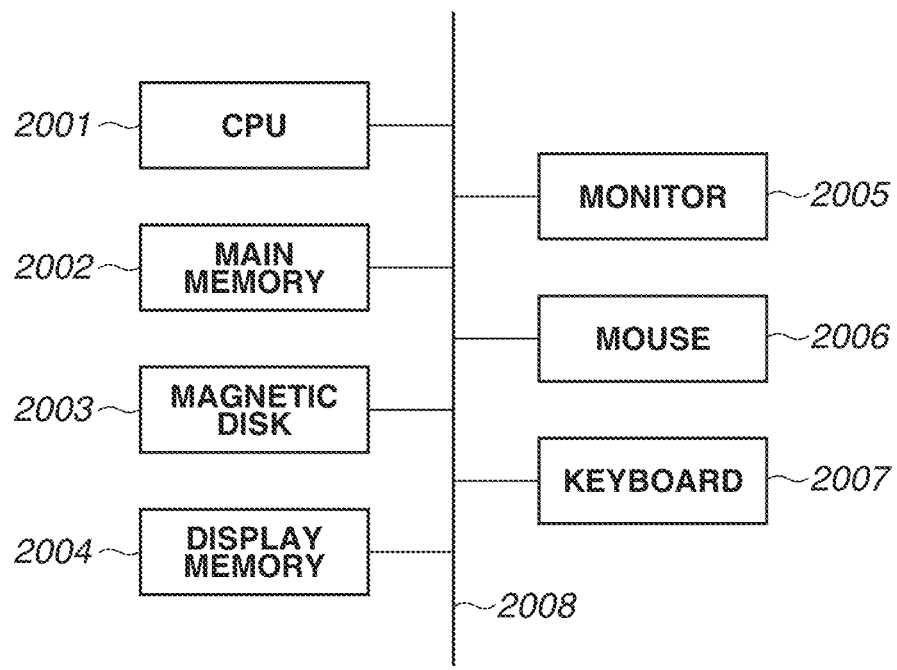
FIG. 2 is a diagram illustrating a hardware configuration example of the information processing apparatus according to the first exemplary embodiment.

FIG. 2 is a diagram illustrating a hardware configuration example of the information processing apparatus 100. A central processing unit (CPU) 2001 mainly controls operations of each constituent element. A main memory 2002 stores therein control programs executed by the CPU 2001 and provides a work area used when the CPU 2001 executes a program. A magnetic disk 2003 stores therein programs to implement various kinds of application software including an operating system (OS), a device driver of a peripheral device, and a program to execute processing to be described below. A display memory 2004 temporarily stores therein data for display. A monitor 2005 is, for example, a cathode-ray tube (CRT) monitor or a liquid crystal monitor, and displays images, texts, and the like on the basis of data from the display memory 2004. A mouse 2006 allows a user to perform pointing input and a keyboard 2007 allows the user to input texts or the like. The constituent elements described above are connected by a common bus 2008 to be able to communicate with one another.

The respective functions (software) of the units of the information processing apparatus 100 illustrated in FIG. 1 and processing in flowcharts described below are implemented by the CPU 2001 executing programs stored in the main memory 2002, the magnetic disk 2003, or the like.

In addition, the CPU 2001 corresponds to an example of a processor. The information processing apparatus 100 may include at least either a graphics processing unit (GPU) or a field-programmable gate array (FPGA) in addition to the CPU 2001. Alternatively, the information processing apparatus 100 may include at least either the GPU or the FPGA, instead of the CPU 2001. The main memory 2002 and the magnetic disk 2003 each correspond to an example of a memory.

Figure 3:
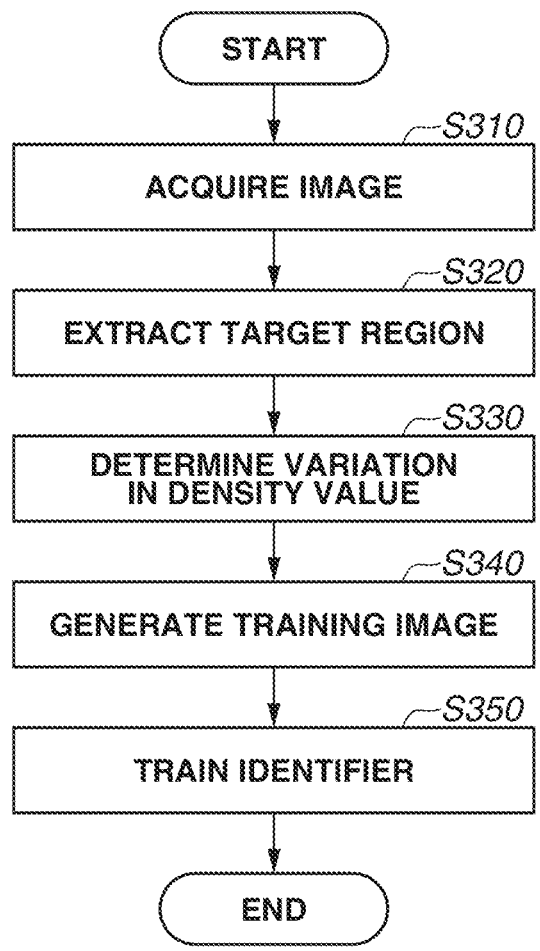
FIG. 3 is a flowchart describing procedures of processing of the information processing apparatus according to the first exemplary embodiment.

Subsequently, procedures of processing of the information processing apparatus 100 according to the present exemplary embodiment will be described below with reference to FIG. 3.

<Step S310>

In step S310, the acquisition unit 101 acquires the training data (the original image and the ground truth data corresponding to the original image) from the storage device 70. That is, the acquisition unit 101 corresponds to an example of an acquisition unit that acquires an image. The training of the U-Net requires a plurality of images. In the present exemplary embodiment, assume that the storage device 70 holds, for example, 1,000 original images, and the acquisition unit 101 acquires the 1,000 original images and respective pieces of ground truth data corresponding to the 1,000 original images.

Figure 4A:
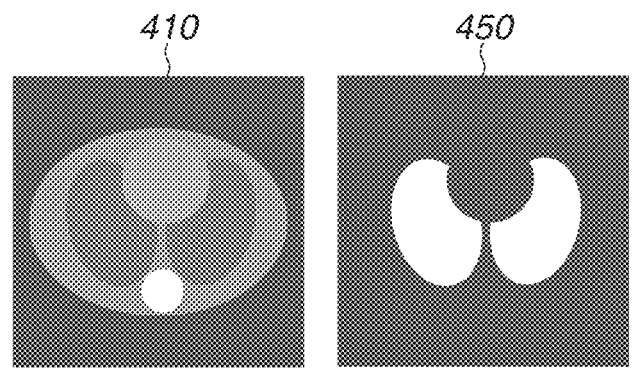
FIG. 4A is a diagram illustrating an example of images according to the first exemplary embodiment.

The original image and ground truth data acquired in step S310 will be described here with reference to FIGS. 4A to 4C. FIG. 4A illustrates a two-dimensional tomographic image 410 indicating the chest and ground truth data 450 corresponding to the two-dimensional tomographic image 410. The two-dimensional tomographic image 410 is one of the two-dimensional tomographic images constituting the three-dimensional tomographic image (original image). In addition, the ground truth data 450 corresponding to the two-dimensional tomographic image 410 is a two-dimensional mask image representing the lung field region.

<Step S320>

In step S320, the extraction unit 102 extracts the target region whose density value is to be changed from each original image in the training data acquired in step S310. In the present exemplary embodiment, the extraction unit 102 extracts a region other than the air region as the target region whose density value is to be changed. That is, the extraction unit 102 extracts a partial region included in the image as the target region. In the three-dimensional tomographic image captured by the X-ray CT apparatus, a density value of the air is almost constant (about −1000 HU). For this reason, the extraction unit 102 extracts the region other than the air region using a threshold processing method in the present exemplary embodiment. Specifically, the extraction unit 102 extracts a region of −550 HU or larger as the region other than the air region, and creates the mask image representing the target region whose density value is to be changed. Alternatively, the information processing apparatus 100 may perform opening processing or closing processing on the region extracted by the method described above or perform deletion processing to delete regions other than a maximum connected region to delete small, isolated regions. The threshold value described above is merely an example and may take any value that enables extraction of the region other than the air region. Alternatively, the extraction unit 102 may extract a region having a density value that is a freely-selected first threshold value or larger as the target region whose density value is to be changed, in the above-described threshold processing. Still alternatively, the extraction unit 102 may extract a region having a density value that is larger than the freely-selected first threshold value as the target region whose density value is to be changed.

Figure 4B:
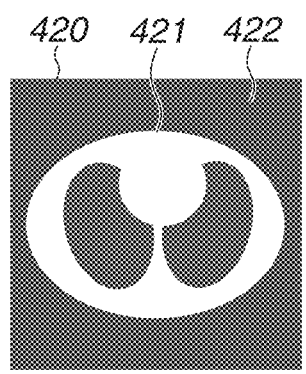
FIG. 4B is a diagram illustrating an example of an image according to the first exemplary embodiment.

In step S320, the extraction unit 102 creates a mask image 420 representing the target region whose density value is to be changed as illustrated in FIG. 4B using the method described above. The mask image 420 is of a size that is the same as that of the two-dimensional tomographic image 410, and holds a target region 421 whose density value is to be changed as a pixel value of 1 and a region 422 other than the target region as a pixel value of 0.

While the description above has been given of the threshold processing method as the method of extracting the target region whose density value is to be changed, the method is not limited thereto. For example, the method may be a level-set method, a graph-cut method, a snake method, or the like, which is a known segmentation method. Besides these methods, the method may be any method of dividing the image into the target region 421 whose density value is to be changed and the region 422 other than the target region. Alternatively, the information processing apparatus 100 may acquire information to differentiate the target region 421 (a mask image or the like) from the outside of the information processing apparatus 100.

<Step S330>

In step S330, on the basis of each original image acquired in step S310 and the mask image representing the target region 421 extracted from the original image in step S320, the determination unit 103 determines density values of the original image in the target region 421. That is, the determination unit 103 corresponds to an example of a determination unit that determines a variation in density value of a pixel included in the image.

A detailed description will be given of a method in which the determination unit 103 determines the variation in density value. In the three-dimensional tomographic image captured by the X-ray CT apparatus, there is a possibility that density values of objects excluding the air and water fluctuate in a range from −50 to +50 HU in accordance with the individual difference among subjects being tested or the image capturing condition. For this reason, the present exemplary embodiment employs a value determined as a random number in the range from −50 to +50 HU as the variation in density value. The variation in density value is not limited to the above.

Alternatively, the determination unit 103 may be configured to further determine an upper limit value and a lower limit value, and determine the variation in density value as a random number in a range not exceeding the upper limit value and the lower limit value. For example, assuming that the upper limit value is +30 HU and the lower limit value is −10 HU, a value of +10 HU between the upper limit value and the lower limit value is determined as the random number as the variation in density value. The numbers described above are merely examples, and the numbers are not limited thereto. Furthermore, the determination unit 103 may be configured to determine only either one of the upper limit value and the lower limit value. Alternatively, the upper limit value and the lower limit value may be automatically determined, or may be determined as a freely-selected value by the user.

In addition, in a case of changing the density value of the target region 421, the determination unit 103 may determine a different variation in density value for each pixel in the target region 421 instead of uniformly using the same variation. That is, the determination unit 103 may determine the variation in density value for each pixel included in the target region 421 on the basis of the density value of each pixel included in the target region 421. In this case, a conceivable method is to use a tone curve to increase a variation in density value of a pixel having a lower density value and decrease a variation in density value of a pixel having a higher density value. Specifically, in a case where density values in the Expression (1), which will be described below, are $x_n^{original} > x_1^{original}$, the determination unit 103 adjusts the tone curve so as to determine a variation c in density value as +10 with respect to the density value of $x_n^{original}$, and determine a variation c in density value as +20 with respect to the density value of $x_l^{original}$.

In a case where the two variations are smaller than 0, the determination unit 103 may decrease an absolute value of the variation in density value of the pixel having the lower density value and increase an absolute value of the variation in density value of the pixel having the higher density value. This can reduce a probability of occurrence of a situation where an image having a density value, which is impossible in an actual image, is generated.

Furthermore, in a case of changing density values of pixels included in the target region 421, the determination unit 103 may determine a partial region including two or more pixels included in the target region 421 and determine a variation in density value in each partial region on the basis of density values of the pixels included in the partial region.

While the determination unit 103 determines only the variation in density value in the target region 421 in the above description, the method of determining the variation in density value is not limited thereto. For example, the determination unit 103 also determines a minute variation in density value with respect to the region 422 other than the target region whose density value is to be changed. In this case, the determination unit 103 may add a value small enough relative to the variation in density value of the target region 421 (e.g., one-tenth of the variation in density value of the target region 421) to a density value of a pixel in the region 422.

That is, the determination unit 103 may be configured to determine both of the variation in density value of the pixel included in the target region 421 and the variation in density value of the pixel included in the region 422 other than the target region. Specifically, the determination unit 103 determines two values such that an absolute value of the variation in density value of the pixel included in the target region 421 is higher than an absolute value of the variation in density value of the pixel included in the region 422 other than the target region, and then generates a training image 430.

That is, a configuration to replace $x_i^{new} = x_i^{original}$ in the Expression (1) with $x_i^{new} = x_i^{original} + c'$ ($c \gg c'$) may be employed.

In a case of creating a training image without changing the density value of the region 422 other than the target region in this configuration, setting c' to zero makes a result equivalent to that in the Expression (1). That is, in the case of creating the training image 430 without changing the density value of the region 422 other than the target region, the determination unit 103 may be configured not to use c' or add c' and set c' to zero.

That is, the determination unit 103 only needs to determine at least the variation c in density value of the pixel included in the target region 421, out of the variation in density value of the pixel included in the target region 421 and the variation in density value of the pixel included in the region 422 other than the target region.

<Step S340>

In step S340, the generation unit 104 generates the training image 430 on the basis of each original image acquired in step S310, the mask image 420 of the target region which is extracted from the original image in step S320 and whose density value is to be changed, and the variation in density value determined in step S330. That is, the generation unit 104 generates the training image 430 in which the density value of the target region 421 whose density value is to be changed has been changed on the basis of the determined variation in density value. More specifically, for example, the generation unit 104 generates the training image 430 by uniformly changing the density values of pixels included in the target region 421 whose density values are to be changed on the basis of the variation in density values determined by the determination unit 103 without changing the density values of pixels included in the region 422 other than the target region.

A method of generating the training image 430 will be described using the Expression (1). In a case where the determination unit 103 determines the variation c in density value, and the density value of the original image is $x^{original}$, the generation unit 104 generates a new training image $x^{new}$ on the basis of the following Expression (1).

[Expression 1]

$$x_i^{new} = \begin{cases} x_i^{original} + c & (i \in T) \\ x_i^{original} & (i \notin T) \end{cases} \quad (1)$$

i represents a pixel number. In addition, T represents a set of pixel numbers added to respective pixels belonging to the target region whose density values are to be changed in the mask image 420 representing the target region whose density values are to be changed. The generation unit 104 performs this calculation with respect to all the original images acquired from the acquisition unit 101. At this time, a value common to all the original images is used as the variation c in density value.

Figure 4C:
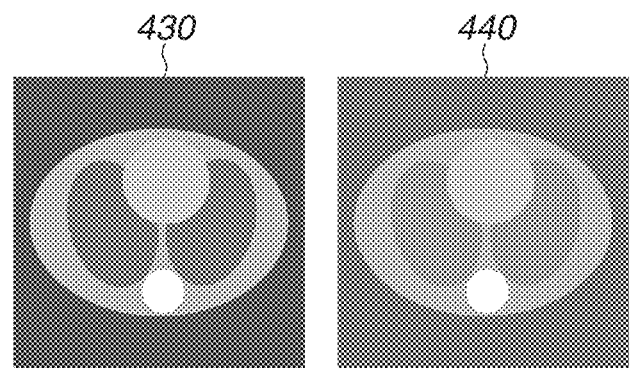
FIG. 4C is a diagram illustrating an example of images according to the first exemplary embodiment.

The generation method described above generates the training image 430 in which only the density values of the target region 421 in the two-dimensional tomographic image 410 are changed as illustrated in FIG. 4C.

Figure 5:
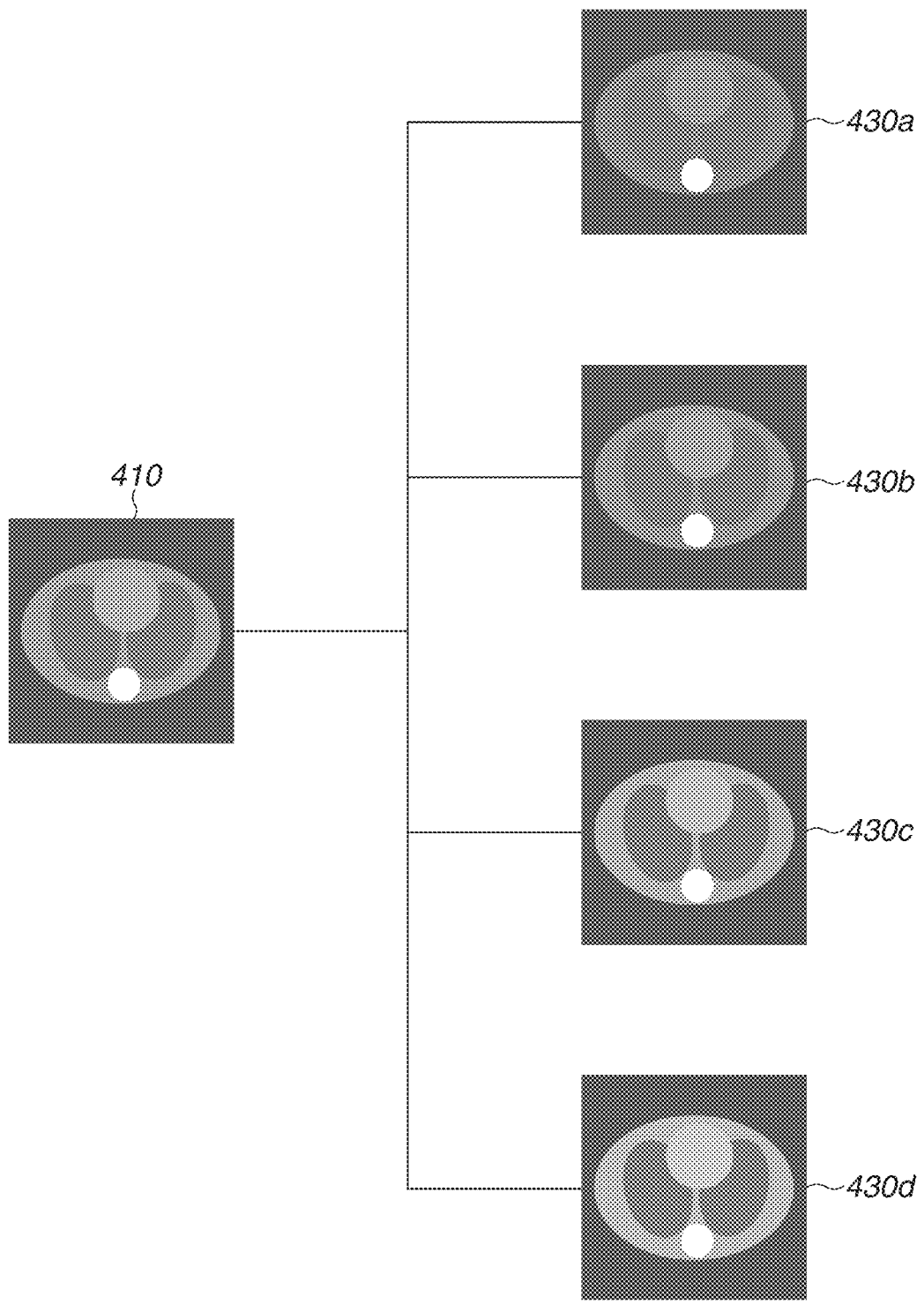
FIG. 5 is a diagram illustrating a method of generating a training image according to the first exemplary embodiment.

The generation unit 104 may generate a plurality of training images 430 from one original image using a plurality of variations c in density values. For example, the generation unit 104 may use four values, such as −20, −10, +10, and +20, as values of variations c in density values to generate four training images 430a to 430d from one two-dimensional tomographic image 410 as illustrated in FIG. 5. The training images 430a to 430d can be obtained by calculating the Expression (1) where c=−20, c=−10, c=10, and c=20, respectively.

In addition, in a case of determining the plurality of variations c in density values as described above, the determination unit 103 may determine the number of density values to be determined on the basis of the number of original images. For example, the determination unit 103 determines five variations c if there are only 2,000 original images with respect to 10,000 pieces of training data to be needed, and two variations c if there are 5,000 original images. As described above, determining the number of variations c on the basis of the number of pieces of data to be needed and the number of original images enables acquisition of the desired number of pieces of data. The above-described number is merely an example, and the number is not limited thereto. Furthermore, the description has been given of the example of increasing the number of variations c as the number of original images decreases with respect to the training data to be needed, but the method of determining the number of variations c is also limited thereto.

Alternatively, a different value of the variation c in density values may be applied to each original image. In a case where the original image is a three-dimensional image, a different value of the variation c in density values may be applied to each two-dimensional image constituting the three-dimensional image. For example, a conceivable method is to generate the training image 430 by applying +10 HU as a variation in density values to the first original image, −20 HU as a variation in density values to the second original image, and a different value as a variation in density values to the next original image or later, in a similar manner.

In addition, the generation of the training image 430 is achieved by various kinds of computing other than the method of generating the training image 430 by adding the variation c to the pixel value of the original image. For example, the generation unit 104 may be configured to multiply the pixel value of the original image by a variation rate a with respect to pixels belonging to the target region 421 to generate the training image 430. In this case, the determination unit 103 determines the variation rate a in step S330.

The generation of the training image 430 without changing the density values of the target region corresponds to the calculation of the Expression (1) where c is zero.

<Step S350>

In step S350, the training unit 105 trains the U-Net on the basis of the training image 430 generated in step S340 and the original image and ground truth data acquired in step S310. The training unit 105 then outputs a result of the training (a parameter of the identifier) to the storage device 70.

The training image 430 newly generated in step S340 is an image in which the density values of the original image have been locally changed. Thus, since the position of the lung field region is unchanged between the original image and the newly generated training image 430, ground truth data that is the same as that corresponding to the original image can be used. Referring to FIGS. 4A to 4C, the ground truth data corresponding to the training image 430 generated in the present exemplary embodiment is the ground truth data 450 corresponding to the two-dimensional tomographic image 410. That is, the training unit 105 generates new training data by adding the training image 430 and the ground truth data (padding data) to the training data acquired in step S310. The training unit 105 then trains the identifier using the newly generated training data.

The backpropagation method, which is a typical method for training of the CNN, is used as a training method. This enables training of the U-Net about complicated characteristics for identifying the target object and performing advanced region extraction from even an unknown image. The training method is not limited thereto.

The training data used for the training of the identifier in step S350 may be any data that includes the training image generated in step S340. For example, the training data used for the training does not necessarily include the original image acquired in step S310.

Furthermore, the training unit 105 may be configured to store the training data used for the training of the identifier in step S350 in the storage device 70. Alternatively, the information processing apparatus 100 may be configured not to perform actual training but perform only processing to store the generated training data as input data to another information processing apparatus that inputs the training data to the identifier to perform the training of the identifier. In this case, the information processing apparatus 100 does not necessarily perform the processing to input the ground truth data corresponding to each original image and the processing to bring the training image 430 into correspondence with the ground truth data.

The information processing apparatus 100 according to the first exemplary embodiment performs the processing following the procedures described above.

Here, a description will be given of a difference between the training image 430 generated by the information processing apparatus 100 according to the first exemplary embodiment and a training image 440 generated by the technology discussed in Patent Literature 1, with reference to FIG. 4C. The training image 430 generated by the information processing apparatus 100 according to the first exemplary embodiment is an image obtained by changing only the density values of the target region 421 in the two-dimensional tomographic image 410. In contrast, the training image 440 generated by the technology described in Patent Literature 1 is an image obtained by uniformly changing density values of the two-dimensional tomographic image 410. As described above, in the X-ray CT apparatus, the density value of the air region is unchanged even if the image capturing condition is changed. Thus, while the technology described in Patent Literature 1 causes a density value that is impossible in reality mainly in the air region, the generation method performed by the information processing apparatus 100 according to the first exemplary embodiment enables correct reproduction of the density value in the air region.

The information processing apparatus 100 according to the first exemplary embodiment differentiates, in the original image, the target region 421 whose density values are to be changed from the region 422 other than the target region whose density values are not to be changed, and changes only the density values of the target region 421 from the original image to generate the new training image. This enables generation of the new training image in consideration of characteristics of the object in the image, thereby increasing accuracy of image recognition of the identifier.

First Modification of First Exemplary Embodiment

In the present exemplary embodiment, the description has been given of the example in which the three regions, i.e., the region as the target of the region extraction by the identifier (the lung field region in the above description), the target region whose density values are to be changed (the human body region excluding the lung field region in the above description), and the region whose density values are not to be changed (the air region in the above description) do not overlap with each other.

However, the advantageous effects of the present exemplary embodiment can be obtained even if these regions overlap with each other. For example, the information processing apparatus 100 may extract the region as the target of the region extraction as a liver region, also the target region whose density values are to be changed as a liver region, and the region whose density values are not to be changed as a region other than the liver region. At this time, the region as the target of the region extraction (the liver region) and the target region whose density values are to be changed (the liver region) overlap with each other. The liver is merely an example, and the target may be an object that is susceptible to fluctuation in density values with a change in image capturing condition, such as the heart or the kidney.

The information processing apparatus 100 according to the first exemplary embodiment performs the following processing on the assumption of such region extraction. The processing in steps S310 and S350 is as described above, and thus a description thereof is omitted. In step S320, the extraction unit 102 acquires the ground truth data from the acquisition unit 101. A region indicated by the ground truth data (the liver region in this example) is set as the target region whose density values are to be changed. That is, the generation unit 104 generates the mask image of the target region on the basis of the ground truth data. In step S330, the generation unit 104 generates the new training image 430 on the basis of the original image acquired in step S310 and the mask image of the target region generated in step S320. The generation method of the training image and the determination method of the variation c in density values are similar to those performed in step S330.

The information processing apparatus 100 according to the present exemplary embodiment generates the training image in which the density values of the target region whose density values are to be changed have been changed. In other words, this is equivalent to the processing of changing the density values of the region as the target of the region extraction. This increases accuracy in image recognition of the identifier in a case of drawing the region as the target of the region extraction with different density values in accordance with the individual difference among subjects being tested or the image capturing condition.

Second Exemplary Embodiment

Regarding the information processing apparatus according to the first exemplary embodiment, the description has been given of the method of increasing/decreasing the density values in the target region using a predetermined value to generate an image. However, there is a possibility that changing the density value in the target region using the predetermined value generates a training image having a density value that is impossible in an actual image.

Thus, an information processing apparatus according to a second exemplary embodiment determines a variation in density values on the basis of density values in a target region whose density values are to be changed, and generates a new training image on the basis of the variation in density values. A difference from the first exemplary embodiment will be described below.

Figure 6:
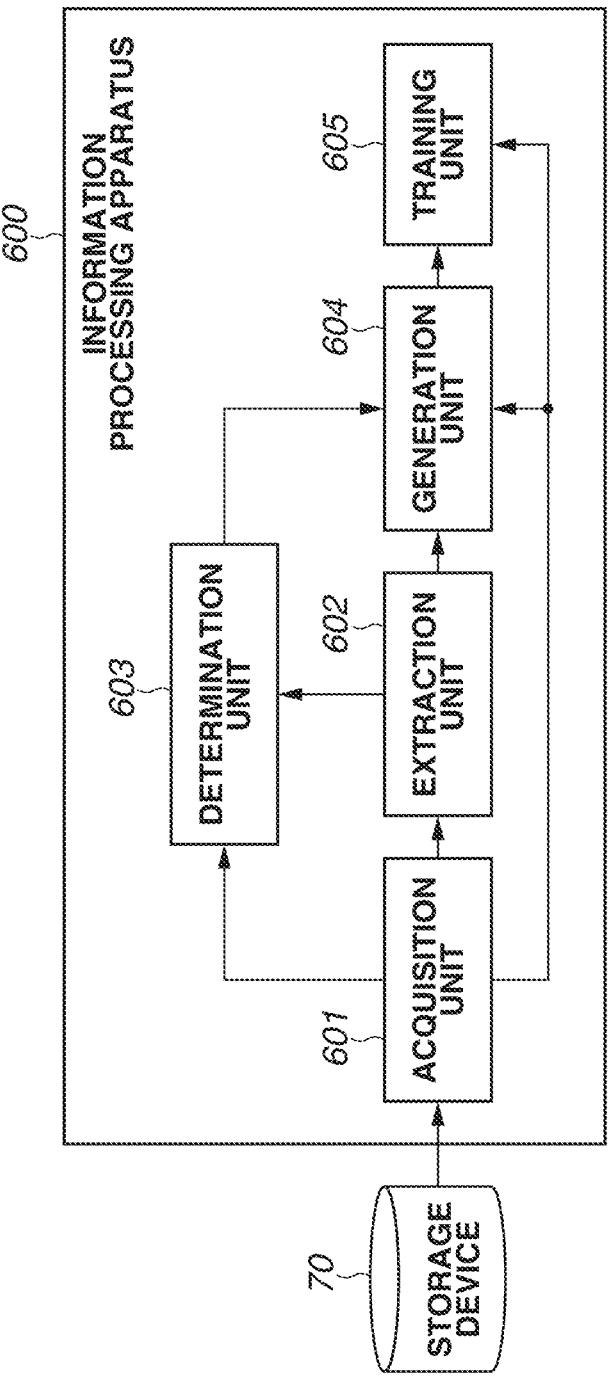
FIG. 6 is a diagram illustrating a configuration example of an information processing apparatus according to a second exemplary embodiment.

A functional configuration of an information processing system according to the present embodiment will be described below with reference to FIG. 6.

An information processing apparatus 600 according to the second exemplary embodiment is composed of an acquisition unit 601, an extraction unit 602, a determination unit 603, a generation unit 604, and a training unit 605. In addition, the information processing system according to the present exemplary embodiment includes the storage device 70 outside the information processing apparatus 600.

Since the information processing system according to the present exemplary embodiment is basically the same as the information processing system according to the first exemplary embodiment, a description of overlapping parts is omitted.

Each unit constituting the information processing apparatus 600 will be described below.

The acquisition unit 601 acquires training data (a set of an original image and ground truth data in correspondence with the original image) from the storage device 70. The acquisition unit 601 then transmits the acquired original image to the extraction unit 602, the determination unit 603, the generation unit 604, and the training unit 605. In addition, the acquisition unit 601 transmits the acquired ground truth data to the training unit 605.

The extraction unit 602 extracts a target region whose density values are to be changed from an image acquired from the acquisition unit 601. The extraction unit 602 then transmits information of the extracted target region to the determination unit 603 and the generation unit 604.

The determination unit 603 determines a variation in density values on the basis of the image acquired from the acquisition unit 601 and the information of the target region acquired from the extraction unit 602. The determination unit 103 then transmits the determined variation in density values to the generation unit 604.

The generation unit 604 generates a new training image on the basis of the image acquired from the acquisition unit 601, the information of the target region acquired from the extraction unit 602, and the variation in density values acquired from the determination unit 603. The generation unit 604 then transmits the generated training image to the training unit 605.

Processing performed by the training unit 605 is similar to that performed by the training unit 105 according to the first exemplary embodiment.

Figure 7:
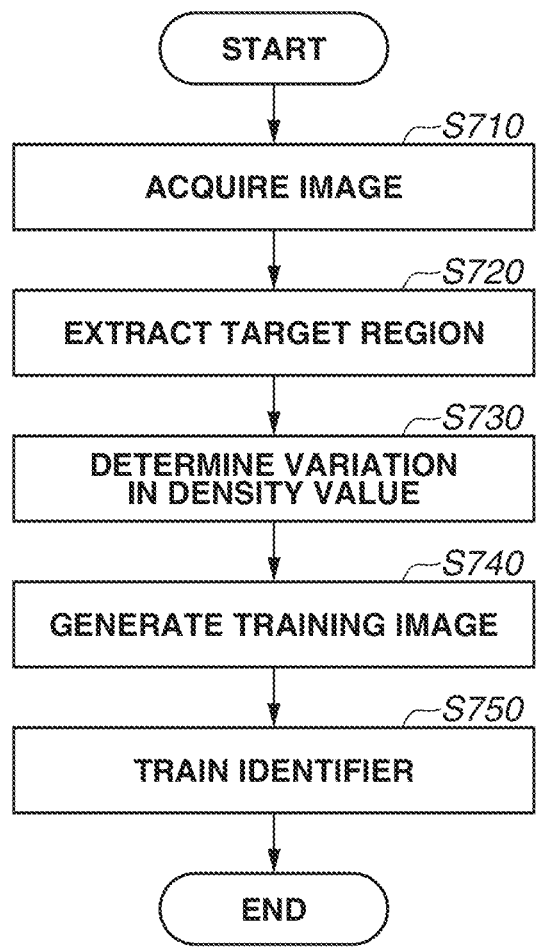
FIG. 7 is a flowchart describing procedures of processing of the information processing apparatus according to the second exemplary embodiment.
Figure 9:
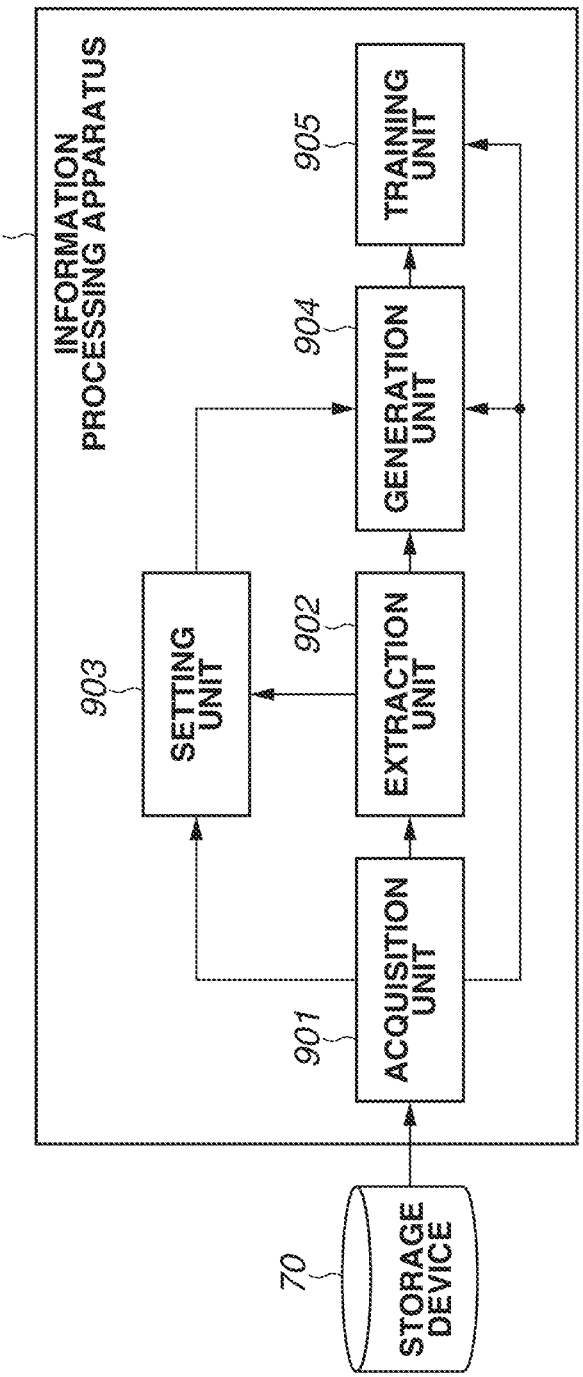
FIG. 9 is a diagram illustrating a configuration example of an information processing apparatus according to a third exemplary embodiment.
Figure 10:
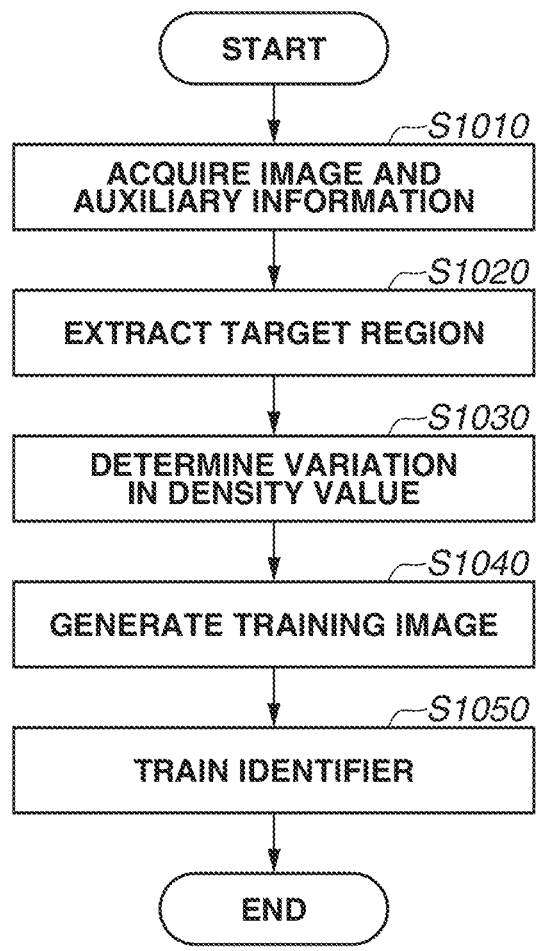
FIG. 10 is a flowchart describing procedures of processing of the information processing apparatus according to the third exemplary embodiment.

Subsequently, procedures of processing of the information processing apparatus 600 according to the present exemplary embodiment will be described below with reference to FIG. 7.

<Steps S710 to S720>

Since processing in steps S710 to S720 is basically the same as the processing in steps S310 to S320 in the first exemplary embodiment, a description thereof is omitted.

<Step S730>

In step S730, the determination unit 603 analyzes density values of the original image in the target region on the basis of each original image acquired in step S710 and the mask image representing the target region 421 extracted from the original image in step S720. The determination unit 603 then determines a variation in density values used for the processing to generate the training image from each original image on the basis of a result of the analysis. Specific examples of a determination method include a method of calculating an average density value of the original image in the target region and determining a variation in density values on the basis of the average density value. For example, the determination unit 603 determines a variation c in density values by referring to a preliminarily prepared correspondence table between an average density value and a variation in density value as illustrated in FIG. 8. For example, in a case where an average density value m of the target region is +17, the determination unit 603 determines six values, such as −40, −30, −20, −10, +10, and +20, as the variation c in density value. The correspondence table as illustrated in FIG. 8 may be the one created with appropriate values determined by a doctor, an engineer, or the like, or may be the one created from statistical information.

<Step S740>

In step S740, the generation unit 604 generates a new training image on the basis of each original image acquired in step S710, the mask image representing the target region extracted from the original image in step S720, and the variation in density values determined in step S730. Specifically, the generation unit 604 changes the density value of each pixel in the target region following the Expression (1) similarly to the processing in step S340 according to the first exemplary embodiment.

<Step S750>

Since processing in step S750 is basically the same as the processing in step S350 in the first exemplary embodiment, a description thereof is omitted.

The information processing apparatus 600 according to the second exemplary embodiment performs the processing following the procedures described above.

The information processing apparatus 600 according to the second exemplary embodiment changes the density values of the target region using the variation in density values determined on the basis of the average density value of the target region to generate the new training image. This enables generation of the new training image in consideration of characteristics of the object in the image, thereby increasing accuracy of image recognition of the identifier.

First Modification of Second Exemplary Embodiment

In the second exemplary embodiment, the description has been given of the method of using the average value of density values of the target region as one example of the method of determining the variation in density values on the basis of the density values of the original image in the target region. However, the method of determining the variation in density values on the basis of the density values of the original image in the target region is not limited thereto. For example, another statistical value of the density values of the target region (e.g., a median value, a variance value, a maximum value, or a minimum value) may be used. For example, using the median value can increase robustness to noise. In any cases, it is possible to determine a variation on the basis of a correspondence table between a preliminarily prepared statistical value and a variation similarly to the correspondence table illustrated in FIG. 8. In addition, besides the method of using the correspondence table, using a freely-selected function to which the statistical value is input and that outputs the variation achieves similar functionality. Furthermore, the statistical value may be a statistical value of density values of part of the target region, instead of the statistical value of density values of the entire target region. For example, the information processing apparatus 600 may select several slice images from a group of two-dimensional tomographic images (slice images) constituting a three-dimensional image, which is the original image, at a predetermined interval or at random, and use a statistical value of density values of the target region in the selected slice images. This reduces processing time in step S730.

Third Exemplary Embodiment

In a third exemplary embodiment, a description will be given of a method of determining a variation in density values on the basis of auxiliary information of an image and generating a training image on the basis of the variation in density values. The present exemplary embodiment employs information regarding a tube voltage in header information of Digital Imaging and Communications in Medicine (DICOM), which is a typical standard of auxiliary information of a medical image, to determine the variation in density values.

In the X-ray CT apparatus, changing the tube voltage varies penetrating power of X-ray beams, and varies density values representing each object. For example, setting the tube voltage to be high increases the X-ray beams having high penetrating power. In this case, an attenuation difference of the X-ray beams is hard to be drawn and the three-dimensional tomographic image tends to be low in contrast. On the contrary, setting the tube voltage to be low decreases the penetrating power of the X-ray beams, thereby making it easy to draw the attenuation difference of the X-ray beams and increasing the contrast of the three-dimensional tomographic image. However, even in the case of capturing the image by changing the tube voltage, the density values of the air and water are unchanged. Therefore, this case is a preferable example to which the present exemplary embodiment is applied.

An information processing apparatus 900 according to the third exemplary embodiment is composed of an acquisition unit 901, an extraction unit 902, a determination unit 903, a generation unit 904, and a training unit 905. In addition, an information processing system according to the present exemplary embodiment includes the storage device 70 outside the information processing apparatus 900.

Since the information processing system according to the present exemplary embodiment is basically the same as the information processing system according to the second exemplary embodiment, a description of overlapping parts is omitted.

Each unit constituting the information processing apparatus 900 will be described below.

The acquisition unit 901 acquires training data (a set of an original image and ground truth data in correspondence with the original image) from the storage device 70. The acquisition unit 901 then transmits the acquired original image to the extraction unit 902, the generation unit 904, and the training unit 905. In addition, the acquisition unit 901 transmits auxiliary information of the image to the determination unit 903 and transmits the ground truth data in correspondence with the image to the training unit 905.

Processing performed by the extraction unit 902 is similar to that performed by the extraction unit 102 according to the first exemplary embodiment.

The determination unit 903 determines a variation in density values on the basis of the auxiliary information of the image acquired from the acquisition unit 901. The determination unit 903 then transmits the determined variation in density values to the generation unit 904.

Processing performed by the generation unit 904 is similar to that performed by the generation unit 604 according to the second exemplary embodiment.

Processing performed by the training unit 905 is similar to that performed by the training unit 105 according to the first exemplary embodiment.

Subsequently, procedures of processing of the information processing apparatus 900 according to the third exemplary embodiment will be described. An overview of the processing is similar to that of the flowchart according to the second exemplary embodiment illustrated in FIG. 7.

<Step S1010>

In step S1010, in addition to the processing in step S310 in the first exemplary embodiment, the acquisition unit 901 acquires auxiliary information of each original image included in the training data, and transmits the original image and the auxiliary information to the determination unit 903.

<Step S1020>

Since processing in step S1020 is basically the same as the processing in step S320 in the first exemplary embodiment, a description thereof is omitted.

<Step S1030>

In step S1030, the determination unit 903 determines a variation in density values to be used for the processing to generate the training image from each original image on the basis of the auxiliary information of each original image acquired in step S1010. In the present exemplary embodiment, a description will be given of an example of a case of using information of the tube voltage in the DICOM header at the time of determining the variation in density values. Specifically, similarly to the processing in step S730 in the second exemplary embodiment, the determination unit 903 determines the variation in density values corresponding to the tube voltage by referring to a preliminarily prepared correspondence table between a tube voltage and a variation in density value.

The auxiliary information used for determination of the variation is not limited to the tube voltage. For example, information about whether a contrast agent has been administered at the time of image capturing. When the X-ray CT apparatus captures a three-dimensional tomographic image after administering the contrast agent to a patient, density values of the organs and the like becomes high. Thus, with respect to an image of a "contrast agent being administered", the determination unit 903 determines a value of the variation in density values such that density values of the training image to be generated are lower than density values of the original image. In addition, with respect to an image of "no contrast agent being administered", the determination unit 903 determines a value of the variation in density values such that the density values of the training image to be generated are higher than the density values of the original image. This can reduce the probability of occurrence of the situation where an image having a density value, which is impossible in an actual image, is generated. Alternatively, the determination unit 903 may determine the variation in density values using contents of a radiologic interpretation report created by a doctor, instead of the DICOM header information. In this case, a conceivable usage example is to determine a larger number of variations in density values with respect to an image for an uncommon diagnostic name that is not easily available, and generate more training images. Besides the above, any auxiliary information regarding the image may be used.

<Step S1040>

Since processing in steps S1040 is basically the same as the processing in step S740 according to the second exemplary embodiment, a description thereof is omitted.

<Step S1050>

Since processing in step S1050 is basically the same as the processing in step S350 in the first exemplary embodiment, a description thereof is omitted.

The information processing apparatus 900 according to the third exemplary embodiment performs the processing following the procedures described above.

The information processing apparatus 900 according to the third exemplary embodiment generates the new training image by changing the density values of the target region using the variation in density values determined on the basis of the auxiliary information of the image. This enables generation of the new training image in consideration of characteristics of the object in the image, thereby increasing accuracy of image recognition of the identifier.

Fourth Exemplary Embodiment

In the first to third exemplary embodiments, the description has been given of the method of generating the new training image by extracting part of the original image as the target region and changing the density values. However, in accordance with an image capturing condition, not only the density values of the entire image vary, but also a contrast between objects may vary or a high and low relationship of the density values of the objects may be reversed. For example, in a three-dimensional tomographic image captured by the X-ray CT apparatus, phase variation over time caused when the contrast agent is administered to a patient corresponds to this phenomenon. In addition, the tube voltage described in the third exemplary embodiment causes a contrast between objects to fluctuate to some extent.

Thus, in the fourth exemplary embodiment, a description will be given of a method of extracting a plurality of target regions whose density values are to be changed and determining a different variation in density values with respect to each target region to generate a new training image. The following description is given of, as a specific example, a case of determining a variation in density values with respect to each target region assuming two regions, a bone region, and a region other than air and bone regions.

Figure 11:
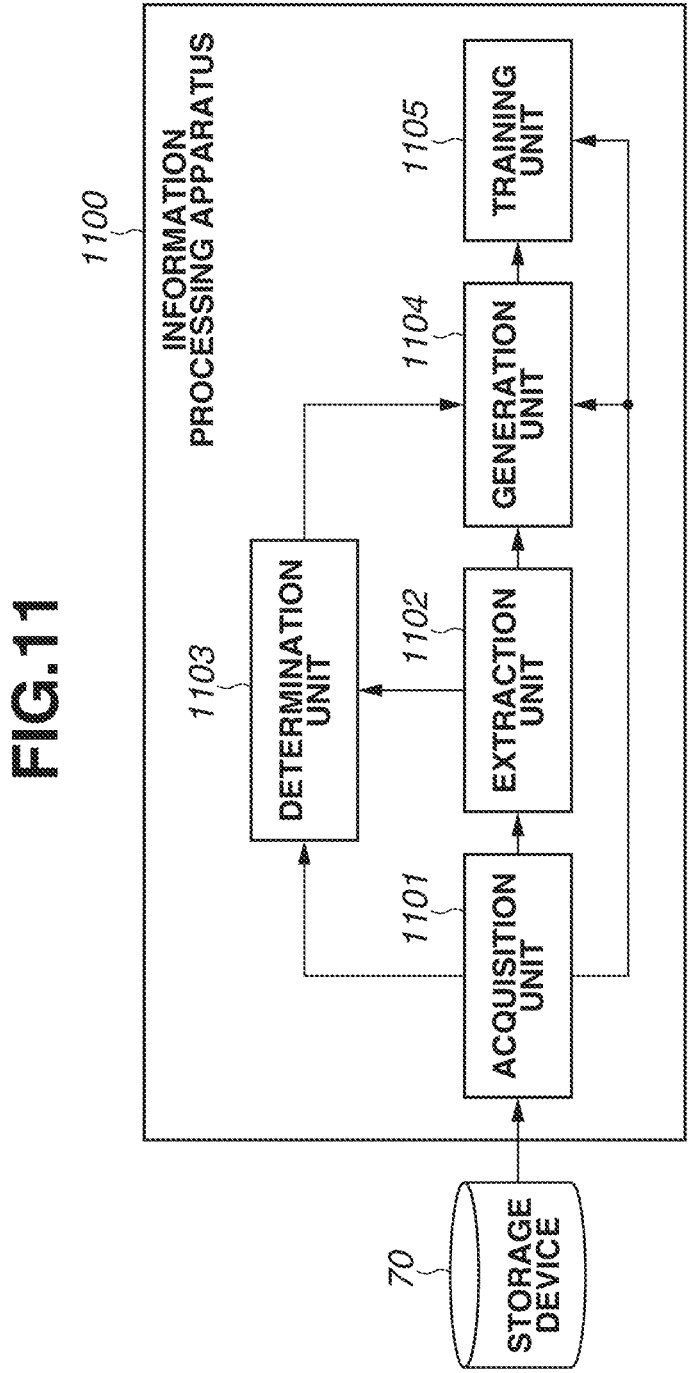
FIG. 11 is a diagram illustrating a configuration example of an information processing apparatus according to a fourth exemplary embodiment.
Figure 12:
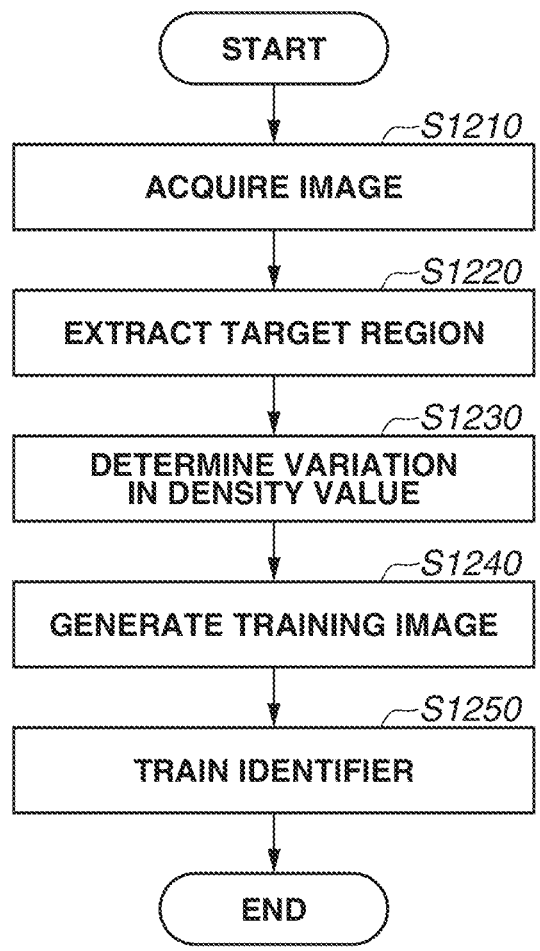
FIG. 12 is a flowchart describing procedures of processing of the information processing apparatus according to the fourth exemplary embodiment.

An information processing apparatus 1100 according to the fourth exemplary embodiment illustrated in FIG. 11 is composed of an acquisition unit 1101, an extraction unit 1102, a determination unit 1103, a generation unit 1104, and a training unit 1105. In addition, an information processing system according to the present exemplary embodiment includes the storage device 70 outside the information processing apparatus 1100.

Since the information processing system according to the present exemplary embodiment is basically the same as the information processing system according to the second exemplary embodiment, a description of overlapping parts is omitted.

Each unit constituting the information processing apparatus 1100 will be described below.

Processing performed by the acquisition unit 1101 is similar to that performed by the acquisition unit 601 according to the second exemplary embodiment.

The extraction unit 1102 extracts a plurality of target regions whose density values are to be changed from the image acquired from the acquisition unit 1101. Specifically, the extraction unit 1102 extracts two or more target regions. The extraction unit 1102 then transmits information of the extracted plurality of target regions to the determination unit 1103 and the generation unit 1104.

The determination unit 1103 determines the variation in density values corresponding to each of the target regions on the basis of the image acquired from the acquisition unit 1101 and the information of the plurality of target regions acquired from the extraction unit 1102. The determination unit 1103 then transmits the determined variation in density values corresponding to each of the determined target regions to the generation unit 1104.

The generation unit 1104 generates a new training image on the basis of the image acquired from the acquisition unit 1101, the information of the plurality of target regions acquired from the extraction unit 1102, and the variation in density values corresponding to each of the plurality of target regions acquired from the determination unit 1103. The generation unit 104 then transmits the generated training image to the training unit 1105.

Processing performed by the training unit 1105 is similar to that performed by the training unit 105 according to the first exemplary embodiment.

Subsequently, procedures of processing performed by the information processing apparatus 1100 according to the present embodiment will be described. An overview of the processing is similar to that of the flowchart according to the second exemplary embodiment illustrated in FIG. 7.

<Step S1210>

Since processing in step S1210 is basically the same as the processing in step S310 in the first exemplary embodiment, a description thereof is omitted.

<Step S1220>

In step S1220, the extraction unit 1102 extracts the two regions, the bone region, and the region other than the air and bone regions, as the target regions whose density values are to be changed from the image acquired in step S1210 to create two mask images. Specifically, the extraction unit 1102 extracts a region having a density value of +600 HU or higher as the bone region and a region having a density value from −550 or higher and below +600 HU as the region other than the air and bone regions using the threshold processing method. At this time, the processing of deleting small, isolated regions on the extracted regions may be added in a similar manner to the processing in step S320 according to the first exemplary embodiment.

The target regions are not limited to the bone region and the region other than the air and bone regions. For example, the information processing apparatus 1100 may acquire region information of each object from the outside of the information processing apparatus 1100 and extract a plurality of target regions to perform more detailed classification. As a specific example, a conceivable method is to create a mask image representing the target region for each organ or each bone in a three-dimensional tomographic image captured by the X-ray CT apparatus, and determine a variation in density values for each organ or each bone. This enables reproduction of the phase variation over time due to the administration of the contrast agent, or the like.

<Step S1230>

In step S1230, the determination unit 1103 determines a variation in density values corresponding to each of the plurality of target regions on the basis of the original image acquired in step S1210 and the mask images of the plurality of target regions extracted in step S1220. Specifically, similarly to the processing in step S730 in the second exemplary embodiment, the determination unit 1103 determines the variation in density values corresponding to each of the regions by referring to the correspondence table between the target region (the bone region and the region other than the air and bone regions) and the variation in density value.

<Step S1240>

In step S1240, the generation unit 1104 generates a new training image on the basis of the original image acquired in step S1210, the mask images of the plurality of target regions extracted in step S1220, and the variation in density values corresponding to each of the target regions determined in step S1230. Specifically, the present exemplary embodiment changes the density value of each pixel in all the target regions following the Expression (1). At this time, the present exemplary embodiment uses the value corresponding to each of the target regions determined in step S1230 as a variation c in density values.

<Step S1250>

Since processing in step S1250 is basically the same as the processing in step S350 in the first exemplary embodiment, a description thereof is omitted.

The information processing apparatus 1100 according to the fourth exemplary embodiment performs the processing following the procedures described above.

The information processing apparatus 1100 according to the fourth exemplary embodiment generates the new training image by extracting the plurality of target regions whose density values are to be changed, and changing the density values of each of the target regions using the variation in density values corresponding to each of the target regions. This enables generation of the new training image in consideration of characteristics of the object in the image, thereby increasing accuracy of image recognition of the identifier.

OTHER EXEMPLARY EMBODIMENT

The disclosure of the present specification can also be achieved by supplying a program that implements one or more functions of the exemplary embodiments described above to a system or an apparatus via a network or a storage medium, and one or more processors in a computer of the system or the apparatus reading and executing the program. Furthermore, the present disclosure can be achieved by a circuit (e.g., an application specific integrated circuit (ASIC)) that implements one or more functions.

The information processing apparatus according to each of the exemplary embodiments described above may be implemented as a single apparatus, or may be configured as a combination of a plurality of apparatuses to be able to communicate with one another and execute the processing described above, which are both included in the exemplary embodiments of the present invention. Alternatively, a common server or a group of servers may execute the processing described above. The information processing apparatus and the plurality of apparatuses constituting the information processing system only need to be capable of communicating with each other at a predetermined communication rate, and are not necessarily located in the same facility or the same country.

The exemplary embodiments in the disclosure of the present specification include an exemplary embodiment in which a software program that implements the functions of the exemplary embodiments described above is supplied to a system or an apparatus, and a computer of the system or apparatus reads out codes of the supplied program to execute the program.

Thus, a program code in itself installed in the computer to implement the processing according to the exemplary embodiments is one of exemplary embodiments of the present invention. In addition, on the basis of an instruction included in the program read out by the computer, an operating system (OS) or the like that operates in the computer may be capable of performing part or all of actual processing and implementing the functions of the exemplary embodiments described above by the processing.

Furthermore, the disclosure of the present specification is not limited to the exemplary embodiments described above, and various modifications (including organic combinations of the exemplary embodiments) can be made on the basis of the gist of the disclosure of the present specification and are not excluded from the scope of the disclosure of the present specification. That is, all configurations of combining any of the exemplary embodiments and modifications thereof are also included in the exemplary embodiments of the disclosure of the present specification.

The present invention is not limited to the exemplary embodiments described above, and various changes and modifications can be made without departing from the spirit and scope of the present invention. Hence, the claims are attached hereto to make the scope of the present invention available to the public.

The disclosure of the present specification enables training of the identifier using new training data whose density values have been changed appropriately.

OTHER EMBODIMENTS

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

The invention claimed is:

1. An information processing apparatus, comprising:
a determination unit configured to extract a region included in an image as a target region, and determine a variation in density value of a pixel included in the target region such that an absolute value of the variation in density value of the pixel included in the target region is larger than an absolute value of a variation in density value of a pixel included in a region other than the target region, wherein the target region is a region whose density value is changeable in accordance with an image capturing condition;
a generation unit configured to generate a training image in which a density value of the pixel included in the target region is changed based on the variation determined by the determination unit; and
a training unit configured to train a identifier using the training image.

2. The information processing apparatus according to claim 1,
wherein the determination unit is configured to determine at least the variation in density value of the pixel included in the target region out of the variation in density value of the pixel included in the target region and the variation in density value of the pixel included in the region other than the target region.

3. The information processing apparatus according to claim 1,
wherein the generation unit is configured to change the density value of the pixel included in the target region based on the variation in density value determined by the determination unit, and generate the training image without changing a density value of the pixel included in the region other than the target region.

4. The information processing apparatus according to claim 1,
wherein the determination unit is configured to determine the variation in density value of the pixel included in the target region and the variation in density value of the pixel included in the region other than the target region.

5. The information processing apparatus according to claim 1,
wherein the determination unit is configured to determine a variation in density value of each of pixels included in the target region based on a density value of a corresponding one of the pixels included in the target region.

6. The information processing apparatus according to claim 1,
wherein the determination unit is configured to determine the variation in density value of the pixel included in the target region based on density values of two or more pixels included in the target region.

7. The information processing apparatus according to claim 1,
wherein the determination unit is configured to determine the variation in density value of the pixel included in the target region based on a statistical value included in the target region.

8. The information processing apparatus according to claim 7,
wherein the statistical value is an average density value of pixels included in the target region.

9. The information processing apparatus according to claim 1,
wherein the determination unit is configured to determine the variation in density value of the pixel included in the target region based on auxiliary information of the image.

10. The information processing apparatus according to claim 1,
wherein the determination unit is configured to further determine at least one of an upper limit value or lower limit value of the variation in density value of the pixel included in the target region, and determine the variation in density value of the pixel included in the target region among values that do not exceed the upper limit value or the lower limit value.

11. The information processing apparatus according to claim 1,
wherein the determination unit is configured to extract two or more of regions as target regions.

12. An information processing apparatus, comprising:
an acquisition unit configured to acquire an image;
an extraction unit configured to extract a region included in the image as a target region, wherein the target region is a region whose density value is changeable in accordance with an image capturing condition;
a determination unit configured to determine a variation in density value of each pixel included in the target region;
a generation unit configured to uniformly change a density value of each pixel included in the target region based on the variation in density value determined by the determination unit and generate a training image without changing a density value of each pixel included in a region other than the target region; and
a training unit configured to train an identifier using the training image.

13. The information processing apparatus according to claim 1,
wherein the image is a medical image.

14. The information processing apparatus according to claim 13,
wherein the target region is a region that is included in the medical image and that is other than an air region.

15. An information processing apparatus, comprising:
an acquisition unit configured to acquire an image; and
a training unit configured to train a identifier using a training image obtained by changing a density value of a pixel included in a first region in the image such that an absolute value of a variation in density value of the pixel included in the first region is higher than an absolute value of a variation in density value of a pixel included in a second region different from the first region in the image, wherein the first region is a region whose density value is changeable in accordance with an image capturing condition.

16. The information processing apparatus according to claim 15,
wherein the training unit is configured to train the identifier using the training image obtained by changing the density value of the pixel included in the first region without changing a density value of the pixel included in the second region.

17. An information processing method, comprising:
extracting a region included in an image as a target region, wherein the target region is a region whose density value is changeable in accordance with an image capturing condition;
generating a training image in which a density value of a pixel included in the target region is changed based on a variation in density value of the pixel included in the target region, the variation being determined to be larger than a variation in density value of a pixel included in a region other than the target region; and
training an identifier using the training image.

18. A non-transitory computer-readable storage medium that stores a program that causes a computer to execute each unit of the information processing apparatus according to claim 1.

* * * * *